(12) United States Patent
Morkin et al.

(10) Patent No.: US 7,504,435 B2
(45) Date of Patent: Mar. 17, 2009

(54) METHOD FOR STIMULATING WEIGHT LOSS AND/OR FOR LOWERING TRIGLYCERIDES IN PATIENTS

(75) Inventors: Eugene Morkin, Punta del Este (UY); Cynthia R. Adamson, legal representative, Punta del Este (UY); Steven Goldman, Tucson, AZ (US)

(73) Assignee: The Arizona Board of Regents on Behalf of the University of Arizona, Phoenix, AZ (US)

( * ) Notice: Subject to any disclaimer, the term of this patent is extended or adjusted under 35 U.S.C. 154(b) by 412 days.

(21) Appl. No.: 11/104,900

(22) Filed: Apr. 13, 2005

(65) Prior Publication Data

US 2008/0146668 A1 Jun. 19, 2008

Related U.S. Application Data

(63) Continuation-in-part of application No. 10/818,541, filed on Apr. 5, 2004, now abandoned, which is a continuation-in-part of application No. 10/368,755, filed on Feb. 18, 2003, now Pat. No. 6,716,877, which is a continuation-in-part of application No. 09/774,994, filed on Jan. 31, 2001, now Pat. No. 6,534,676.

(51) Int. Cl.
*A61K 31/19* (2006.01)
*C07C 65/00* (2006.01)
*C07C 229/00* (2006.01)

(52) U.S. Cl. .................. 514/557; 514/568; 562/405; 562/447; 562/472

(58) Field of Classification Search ............. 562/405, 562/472, 447; 514/557, 568
See application file for complete search history.

(56) References Cited

U.S. PATENT DOCUMENTS

| | | | |
|---|---|---|---|
| 2,803,654 A | 8/1957 | Anthony et al. | 260/519 |
| 3,102,136 A | 8/1963 | Meltzer | |
| 3,109,023 A | 10/1963 | Weil | 260/515 |
| 3,149,153 A | 9/1964 | Blank et al. | |
| 4,451,465 A | 5/1984 | White et al. | 424/251 |
| 4,772,631 A | 9/1988 | Holloway et al. | 514/539 |
| 4,977,148 A | 12/1990 | Holloway et al. | 514/183 |
| 4,999,377 A | 3/1991 | Caulkett et al. | 514/507 |
| 5,158,978 A * | 10/1992 | Rubin | 514/567 |
| 5,284,971 A | 2/1994 | Walker et al. | 562/429 |
| 5,883,294 A | 3/1999 | Scanlan et al. | 562/471 |
| 6,017,958 A | 1/2000 | Kun et al. | 514/532 |
| 6,221,911 B1 | 4/2001 | Lavin et al. | 514/567 |
| 6,534,676 B2 | 3/2003 | Morkin et al. | 562/405 |
| 6,716,877 B2 | 4/2004 | Morkin | |
| 6,951,844 B2 | 10/2005 | Hangeland | |
| 2003/0147815 A1 | 8/2003 | Morkin | 424/45 |

FOREIGN PATENT DOCUMENTS

| | | |
|---|---|---|
| DE | 1078582 B | 3/1960 |
| WO | WO 00/39077 | 7/2000 |
| WO | WO-02/060389 A2 | 8/2002 |
| WO | WO-02/060389 A3 | 8/2002 |
| WO | WO-2004/073694 A1 | 9/2004 |
| WO | WO 2005/009433 | 2/2005 |
| WO | WO-2005/097102 A2 | 10/2005 |
| WO | WO-2005/097102 A3 | 10/2005 |

OTHER PUBLICATIONS

Deirdre M. B. Hickey et al, "Synthesis of Thyroid Hormone Analogues. Part 3. Iodonium Salt Approaches to SK&F L-94901", J. Chem. Soc., Perkin Trans. I, (1988), pp. 3103-3111.*
"Pilot Studies on the Use of 3,5-Diiodothyropropionic Acid, A Thyroid Hormone Analog, in the Treatment of Cnogestive Heart Failure" Morkin et al., *Clinical Pharacology*, Dec. 3, 2001, pp. 218-225.
"Cardiac Effects of 3,5-Diiodothyropionic Acid, a Thyroid Hormone Analog with Inotropic Selectivity" Pennock et al., *The Journal of Pharmacology and Experimental Therateutics*, vol. 263, No. 1, 1992, pp. 163-169.
"The Metabolic Effects of the Acetic and Propionic Acid Analogs of Thyroxine and Triiodothyronine" Hill et al., *J. Clin. Invest.*, Vo. 39, 1960, pp. 523-533.
"Synthesis and Physiological Activity of Some New Analgues of Thyroxine" *Endocrinology*, Vo. 66, 1960, pp. 628-630.
"The Physiological Disposition in the Rat of the Acetic and Propionic Acid Analogues of Thyroxine and Triiodothyronine" Hatfield et al., *Endocrinology*, vol. 66, 1960, pp. 676-693.
"Comparative Effects of Thyroxine Analogues in Experimental Animals" Money et al., *Annals New York Academy of Sciences*, vol. 86, 1960, pp. 512-545.
"Analogues and Derivatives of Thyroxine: Their Physiolgic Effects and Possible Pharmacotherateutic Roles in Clinical Medicine" Rawson, *Adv. Intern. Med.*, Vo. 11, 1962, pp. 215-233.
Matsuura T., Synthesis 3,5,3',5'Hhalogen-Substituted ThyropropionicAacids, J Med Chem 1964;830-831.
Supplementary European Search Report mailed on May 7, 2007, for EP Application No. 03777748.9, four pages.
Barker, S.B. et al. (Jan. 1951). "Metabolic Effects of Some Halogenated Acrylic Acid Analogues of Thyroxine," *Endocrinology* 48(1):70-74.
Barnes, J. H. et al. (1950). "The Synthesis of Thyroxine and Related Substances. Part VII. The Preparation of Diphenyl Ethers from 2, 6-Diiodophenols," *The Journal of the Chemical Society*, pp. 2824-2833.
Beringer, F. M. et al. (1959). "Diaryliodonium Salts- (IX) Synthesis of Substituted Diphenyliodonium Salts," *Journal of the American Chemical Society* 81:342-350.
Clayton, J. C. et al. (1951). "Synthesis of Thyroxine and Related Substances. VIII. The Preparation of Some Halogeno-and Nitrodiphenyl Ethers," *Journal of the Chemical Society*, pp. 2467-2473.

(Continued)

Primary Examiner—Taylor Victor Oh
(74) *Attorney, Agent, or Firm*—Morrison & Foerster LLP

(57) ABSTRACT

Administration of a therapeutically effective amount of 3,5-diiodothyropropionic acid stimulates weight loss in patients, lowers triglyceride levels and reduces risk of death or progression of coronary heart disease in patients with metabolic syndrome.

29 Claims, No Drawings

OTHER PUBLICATIONS

Eades, C. H., Jr. et al. (1963). "Effect of Thyropropionic Acid and Its Iodinated Analogues on Incorporation of Acetate-1-$C_{14}$ Into Cholesterol by Rat Liver Homogenates," *Endocrinology* 72(4):514-517.

Pennock, G.D. et al. (Jan. 1994). "Identification of Simple Substituted Phenols with Thyromimetic Activity: Cardiac Effects of 3,5-Diiodo-4-Hydroxyphenylpropionic Acid," *Journal of Pharmacology and Experimental Therapeutics* 268(1):216-233.

Supplementary European Search Report mailed on May 19, 2006 for EP Application No. 02709310.3, six pages.

International Search Report mailed on Jun. 11, 2008, for PCT Application No. PCT/US08/02680, filed on Feb. 27, 2008, 1 page.

Written Opinion mailed on Jun. 11, 2008, for PCT Application No. PCT/US08/02680, filed on Feb. 27, 2008, 5 pages.

Morken, et al., "Studies on the Use of Thyroid Hormone and a Thyroid Hormone Analogue in the Treatment of Congestive Heart Failure", The Society of Thoracic Surgeons, 1993, Sections 54-60.

Pennock, et al., "Combination Treatment with Captopril and the Thyroid Hormone Analogue 3,5-Diiodothyropropionic Acid", Circulation, 1993, pp. 1289-1298.

Mahaffey, et al., "Left Ventricular Performance and Remodeling in Rabbits after Myocardial Infarction", American Heart Association, 1994, pp. 794-801.

Morkin, et al., "Development of a Tyroid Hormone Analogue for the Treatment of Congestive Heart Failure", Symposium on Novel Actions of Thyroid Hormone, 1996, pp. 521-526.

Spooner, et al., "Thyroid Hormone and Thyroid Hormone Analogues in the Treatment of Heart Failure", Lippincott Williams & Wilkins, 1999, pp. 395-399.

Pennock, et al., "Prevention of Abnormal Sarcoplasmic Reticulum Calcium Transport and Protein Expression in Post-infarction Heart Failure Using 3,5-Diiodothyroipropionic Acid (DITPA)", Academic Press, 2000, pp. 1939-1953.

"Metabolic Effects and Therapeutic Applications of Triiodothyropropionic Acid" Leeper et al., *Clin. Pharmacol. Ther.* 2, pp. 13-21, 1961.

"Synthesis and Biolobical Activity of Some Triiodinated Analogues of Thyroxine" Tomita et al., *J Biol Chem 219*, pp. 595-604, 1956.

"The Preparation of Thyroxine Analogs" Wawzonek et al., *J. Organic Chem 15*, pp. 593-599, 1950.

"The Effect of Various Thyroxine Analogues on Suppression of 1 131 Uptake by the Rat Thyroid", Money et al., *Endocrinology 64*, pp. 123-125, 1959.

Blank B Pfeiffer FR, Greenberg CM, Kerwin JF, Thyromimetics. I., The synthesis and hypocholesteremic activity of some 3' and 3',5'-Alryl and Aryl-3,5-Diiodothyronines, J Med Chem 1963; 6:554-560.

Blank B, Pfeiffer FR, Greenberg, CM, Kerwin JF, Thyromimetics. II., The Synthesis and Hypocholesteremic Activity of Some b-Diethylaminoethyl esters of Iodinated Thyroalkaonic Acids, J Med Chem 1963;560-563.

Leeson PD, Ellis D, Emmett JC, Shah VP, Showell GA, Underwood AH, Thyroid Hormone Snalogues. Synthesis of 3'-Substituted 3,5-Diiodo-L-Thyronines and Quantitative Structure-Activity Studies of in Vitro and in Vivo Thyromimetic Activities in Rat Liver and Heart, J Med Chem 1988;31:37-54.

Hamilton MA, Stevenson LW, Fonarow GC, Steimle A, Goldhaber JI, Child JS, Chopra IJ, Moriguchi JD, Hage A. Safety and hemodynamic effect of Intravenous trilodothyronine in advanced congestive heart failur, Am J Cardiol 1998;81:443-47.

Moruzzi P, Doria E, Agostoni PG, Capacchione V, Sganzeria, PG, Usefulness of L-Thyroxine to Improve Cardiac and Exercise Performance in Dilated Cardiomyopathy, Am J Cardiol 1994;73:374-78.

Moruzzi P, Doria E, Agostoni PG, Medium-Term Effectiveness of L-Thyroxine Treatment in Idiopathic Dilated Cardiomyopathy, Am J Med 1996;101:461-7.

Pennock GD, Raya TE, Bahl JJ, Goldman S, Morkin E, Cardiac Effects of 3,5-Diiodothyropropionic Acid, a Thyroid Hormone Analog with Inotropic Selectivity, J Pharmacol Exp Ther 1992;263:163-9.

Mahaffey KW, Raya TE, Pennock GF, Morkin E, Goldman S., Left Ventricular Performance and Remodeling in Rabbits After Myocardial Infarction. Effects of a Thyroid Hormone Analogue, Circulation 1995;91:794-801.

Pennock GD, Raya TE, Bahl JJ, Goldman S, Morkin E., Combination Treatment with Captopril and the Thyroid Hormone Analogue, 3,5-Diiodothyropropionic Acid. A New Approach to Improving Left Ventricular Performance in Heart Failure, Circulation 1993;88:1289-98.

Goldman S, Olajos M, Morkin E., Control of Cardiac Output in Thyrotoxic Calves. Evaluation of Changes in Systemic Circulation, J Clin Invest 1984;73:358-65.

Asanol H, Ishizuka S, Joho S, Kameyama T, Inoue H, Sasayama S. , Altered Inotropic and Lusitropic Responses to Heart Rate in Conscious Dogs with Tachycardia Induced Heart Failure, J Am Coll Cardiol 1996;27:728-35.

Mulleri LA, Hasenfuss G, Leavitt B, Allen PD, Alpert NR., Altered Myocardial Force-Frequency Relation in Human Heart Failure, Circulation 1992;85:1743-50.

13. Litwin SE, Zhang D, Roberge P, Pennock GD., DITPA Prevents the Blunted Contraction-Frequency Reiationship in Myocytes from infarcted Hearts, Am J Physiol (Heart and Circ Physiol) 2000;278:H862-70.

Khoury SF, Hoit BD, Vrushank D, Pawloski-Dahm CM, Shao Y, Gabel M, Periasamy M, Walsh RA, Effects of Thyroid Hormone on Left Ventricular Performance and Regulation of Contractile and Ca2+ Cycling Proteins in the Baboon. Implications for the Force-Frequency and Relaxation-Frequency Relationship, Circ Res 1996;79:727-35.

Hoit BD, Pawloski-Dahm CM, Shao Y, Gabel M, Walsh RA, The Effects of a Thyroid Hormone Analog on Left Ventricular Performance and Contractile and Calcium Cycling Proteins in the Baboon, Proc Assoc Am Physicians 1997; 109:136-45.

Tomanek RJ, Zimmerman MB, Survarna PR, Morkin E, Pennock GD, Goldman S., A Thyroid Hormone Analog Stimulates Angiogenesis in the Post Infarction Rat Heart, J Mol Cell Cardiol 1998;30:923-32.

Matsuura, T., Synthesis of 3,5,3',5'Hhalogen-Substituted ThyropropionicAacids, J Med Chem 1964;830-831.

"Clinical and Experimental Sudies on the Use of 3,5-Diiodothyropropionic Acid, a Thyroid Hormone Analogue, in Heart Failure" Morkin et al., *Thyroid*, vol. 12, No. 6, 2002, pp. 527-533.

"Left Ventricular Performance and Remodeling in Rabbits After Myocardial Infarction" Mahaffey et al., Circulation vol. 91, No. 3, 1995, pp. 794-801.

"Combination Treatment with Captopril and the Thyroid Hormone Analogue 3,5-Diiodothyropropionic Acid" Pennock et al., Circulation Vo. 88, No. 3, 1993, pp. 1289-1298.

"A Dissociation of Thyroid Hormonal Effects by Structural Alterations of the Thyroxine Molecule" Rawson et al., *The American Journal of the Medical Sciences*, 238, 1959, pp. 267-273.

Mechanisms of Thyroid Hormone Action: Insights from X-Ray Crystallographic and Functional Studies: Ribeiro et al, *Recent Progress in Hormone Research*, Vo. 53, 1998, pp. 351-394.

"Metabolic Effects and Therapeutic Applications of Triiodothyropropionic Acid" Leeper et al., *Clin. Pharmacol. Ther.*, vol. 2, 1961, pp. 13-21.

"The Preparations of Thyroxine Analogs" Wawzonek et al., *Journal Organic Chemistry*, vol. 15, 1950, pp. 593-599.

"The Effect of Various Thyroxine Analogues on Suppression I 131 Uptake by the Rat Thyroied" Money et al., *Endocrinology*, vol. 64, 1959, pp. 123-125.

"Synthesis and Biological Activity of Some Thiiodinated Analogues of Thyroxine" Tomita et al., *Journal of Biological Chemistry*, Vo. 219, 1956, pp. 595-604.

"Antigoitrogenic and Calorigenic Activities of Thyroxine Analogues in Rats" Stasilli et al., *Endocrinology*, vol. 64, 1959, pp. 62-82.

"The Binding to Serum Protein of Acetic and Propionic Acid Anaglogues of Thyroxine and Triiodothyronine" Christensen, *Endocrinology*, vol. 67, 1960, pp. 407-412.

"Depression of the Serum Cholesterol Level By Triioidothyropropionic Acid" *Journal of Enocrin. Metab.*, vol. 19, 1959, pp. 490-193.

Asanoi, H. et al. (1996). "Altered Inotropic and Lustitropic Responses to Heart Rate in Conscious Dogs with Tachycardia Induced Heart Failure," *J. Am. Coll. Cardiol.* 27:728-735.

Blank, B. et al. (1963). "Thyromimetics. I. The Synthesis and Hypocholesteremic Activity of Some 3' and 3', 5'-Alryl and Alryl-3,5-Diiodothyronines," *J. Med. Chem.* 6:554-560.

Blank, B. et al. (1963). "Thyromimetics. II., The Synthesis and Hypocholesteremic Activity of Some b-Diethylaminoethyl esters of Iodinated Thyroalkanoic Acids," *J. Med. Chem.* pp. 560-563.

Goldman, S. et al. (1984). "Control of Cardiac Output in Thyrotoxic Calves. Evaluation of changes in Systemic Circulation," *J. Clin. Invest.* 73:358-365.

Hamilton, M.A. et al. (1998). "Safety and hermodynamic effect of Intravenous triiodothyronine in advanced congestive heart failure," *Am. J. Cardiol.* 81:443-447.

Hoit, B.D. et al. (1997). "The Effects of a Thyroid Hormone Analog on Left Ventricular Performance and Contractile and Calcium Cycling Proteins in the Baboon," *Proc. Assoc. Am. Physicians* 109:136-145.

Khoury, S.F. et al. (1996). "Effects of Thyroid Hormone on Left Ventricular Performance and Regulation on Contractile and Ca2+ Cycling Proteins in the Baboon. Implications for the Force-Frequency and Relaxation-Frequency Relationship," *Circ. Res.* 79:727-735.

Leeson, P.D. et al. (1988). "Thyroid Hormone Analogues, Synthesis of 3'-Substituted 3,5-Diiodo-L-Thyronines and Quantitative Structure-Activity Studies of in Vitro and in Vivo Thyromimetic Activites in Rat Liver and Heart," *J. Med. Chem.* 31:37-54.

Litwin, S.E. et al. (2000). "DIPTA Prevents the Blunted Contraction-Frequency Relationship in Myocytes from Infracted Hearts," *Am. J. Physiol. (Heart and Circ. Physiol.)* 278:H862-H870.

Mahaffey, K.W. et al. (1995). "Left Ventricular Performance and Remodeling in Rabbits After Myocardial Infraction. Effects of a Thyroid Hormone Analogue," Circulation 91:794-801.

Morkin et al. (1993). "Studies on the Use of a Thyroid Hormone and a Thyroid Hormone Analogue in the Treatment of Congestive Heart Failure," The Society of Thoraic Surgeons 56(1)S54-S60.

Morkin et al. (1996). "Development of a Thyroid Hormone Analogue for the Treatment of Congestive Heart Failure," Symposium on Novel Actions of Thyroid Hormone 6(5):521-526.

Moruzzi, P. et al. (1994). "Usefulness of L-Thyroxine to Improve Cardiac and Exercise Performance in Dilated Cardiomyopathy," *Am. J. Cardiol.* 73:374-378.

Moruzzi, P. et al. (1996). "MediumTerm Effectiveness of L-Thyroxine Treatment in Idiopathic Dilated Cardiomyopathy," *Am. J. Med.* 101:461-467.

Mulieri, L.A. et al. (1992). "Altered Myocardial Force-Frequency Relation in Human Heart Failure," Circulation 85:1743-1750.

Pennock et al. (2000). "Prevention of Abnormal Sarcoplasmic Reticulum Calcium Transport and Protein Expression in Post-Infraction Heart Failure Using 3,5-Diiodothyropropionic Acid (DITPA)," Academic Press, pp. 1939-1953.

Sponner P.H. et al. (1999). "Thyroid Hormone and Thyroid Hormone Analogues in the Treatment of Heart Failure," Lippincott Williams & Wilkins, pp. 395-399.

Tomanek, R.J. et al. (1998). "A Thyroid Hormone Analog Stimulates Angiogenesis in the Post Infraction Rat Heart," *J. Mol. Cell. Cardiol.* 30:923-932.

* cited by examiner

METHOD FOR STIMULATING WEIGHT LOSS AND/OR FOR LOWERING TRIGLYCERIDES IN PATIENTS

CROSS REFERENCE TO RELATED APPLICATION

This application is a continuation-in-part of application Ser. No. 10/818,541, filed Apr. 5, 2004 now abandoned, which is, in turn a continuation-in-part of U.S. application Ser. No. 10/368,755, filed Feb. 18, 2003, now U.S. Pat. No. 6,716,877 issued Apr. 6, 2004, which is, in turn a continuation-in-part of U.S. application Ser. No. 09/774,994, filed Jan. 31, 2001, now U.S. Pat. No. 6,534,676, issued Mar. 18, 2003.

BACKGROUND OF THE INVENTION AND DISCUSSION OF THE PRIOR ART

Researchers at the Centers for Disease Control and Prevention (CDC) estimated that as many as 47 million Americans may exhibit a cluster of medical conditions (a "metabolic syndrome") characterized by abdominal obesity, hypertriglyceridemia, low high-density lipoprotein (HDL) cholesterol, high blood pressure, and elevated fasting blood glucose [1]. Having three or more traits of metabolic syndrome significantly increases the risk of dying from coronary heart disease or cardiovascular disease. It has also been reported that patients with even one or two metabolic syndrome traits, or those with metabolic syndrome but without diabetes also were at increased risk for death from coronary heart disease or cardiovascular disease.

Obesity and atherosclerosis have a major impact on morbidity and mortality in the United States and many other countries. Elevated cholesterol, particularly low-density lipoprotein (LDL) cholesterol, is a major risk factor for atherosclerosis. Thyroid hormone replacement in hypothyroid individuals reduces total cholesterol and LDL-cholesterol [2-4]. An excess of thyroid hormone in thyrotoxicosis causes weight loss. The weight loss consists not only of fat but also muscle mass and even myopathy can be observed [5].

The ability of thyroid hormone to lower cholesterol when given to hypothyroid individuals prompted efforts to design analogs that take advantage of these properties in the treatment of hypercholesterolemia. This action is the result of an accelerated LDL-cholesterol clearance rate [6-8]. $T_3$ increases levels of both the hepatic LDL receptor [9] and its mRNA [10]. Additional thyroid hormone actions on lipid metabolism include increasing the activity of lipoprotein lipase [11].

Numerous studies have been carried out to synthesize thyroid hormone analogs that mimic the actions of the natural hormones. The objective of most of these efforts has been to develop thyromimetics that lower plasma cholesterol without adverse cardiac effects. A series of thyroxine analogs and methods of synthesis are described in U.S. Pat. No. 3,109,023. Thyroid hormone agonists that are highly selective for the thyroid hormone receptor (TR) β-subtype are described in U.S. Pat. No. 5,883,294 and WO 00/39077. U.S. Pat. No. 5,284,971 describes a class of thyromimetics, which have the distinguishing characteristic of a sulfonyl bridge in the diphenyl core.

The usual method employed in treating obesity has been reduction of caloric intake either by reduced caloric diet or appetite suppression. An alternative method is to stimulate metabolic rate in adipose tissue. For example U.S. Pat Nos. 4,451,465, 4,772,631, 4,977,148 and 4,999,377 disclose compounds possessing thermogenic properties at dosages causing few or no deleterious side-effects, such as cardiac stimulation. Further pharmaceutical compositions including those selective for the β-type thyroid hormone receptor have been taught by Cornelius et al. in US 2002/0035153 A1. A representative compound of this type, N-[4-[3'[(4-fluorophenyl)hydroxymethyl]-4'-hydroxyphenoxy]-3,5-dimethylphenyl]oxamate (CGS-26214) reportedly is devoid of significant cardiovascular effects but possess significant thermogenic properties. Accordingly, CGS-26214 and related compounds are useful in the treatment of obesity and related conditions in humans and companion animals. According to Cornelius et al. compounds related to CGS-26214 may be combined with an anorectic agent such as phenylpropanolamine, ephedrine, pseudoephedrine, phentermine, a Neuropeptide Y antagonist, a cholecystokinin-A agonist, etc. Whereas administration of a selective β-agonist would compensate for endogenous hormones in terms of TRβ stimulation it may not significantly activate TRα, which could cause a relative hypothyroidism or could cause increased hepatic toxicity. Also, there is no information on whether weight loss would be selective for fat or would include muscle as well.

Goglia and Lanni in WO2005009433 describe the use of a breakdown product of thyroid hormone (3,5-diiodothyronine) as a regulator of lipid metabolism to stimulate burning of fatty acid in mitochondria. $T_3$, which is largely derived from $T_4$ by the action of monodeiodinases, has been thought to be the major active form of thyroid hormone. It has been reported that 3,5-diiodothyronine (3,5-$T_2$) is able to directly increase mitochondrial respiration by increasing the burning of fatty acids. In keeping with the stimulation of mitochondrial respiration, fatty acid oxidation rate was increased by 3,5-$T_2$. In rats fed a high-fat diet long-term treatment with 3,5-$T_2$ reportedly decreased weight gain. These effects were observed without suppression of TSH or evidence of hyperthyroidism. 3,5-$T_2$ also was given to four volunteers in daily doses between 15 and 90 microgram/kg. There was a reduction in plasma levels of triglycerides from 140-70 mg/dL and cholesterol from 241 mg/dL to 210 mg/dL. The resulting metabolic rate increased in a dose dependent manner reaching a maximum increase of 40% (from 1770 Kcal to 2400 Kcal per day). Fat mass was reduced in the range of 10 to 15%. There was no significant change in plasma levels of free $T_3$ and free $T_4$.

The actions of 3,5-$T_2$ and $T_3$ on mitochondrial respiration can be distinguished by differences in the time course of the response [12]. Changes in resting metabolic rate in hypothyroid rats treated with a single injection of 3,5-$T_2$ started 6-12 hours after infection with the maximal stimulation at 28-30 hours. By contrast injection of $T_3$ increased resting metabolic rate that started 25-30 hours after injection and lasted 5-6 days. At the mitochondrial level stimulation is very rapid after injection of 3,5-$T_2$, occurring within 1 hour.

In my parent application, now U.S. Pat. No. 6,534,676, I describe and claim the use of a thyroid hormone analog 3,5-diiodothyropropionic acid (DITPA) for treating patients with congestive heart failure. More particularly, as reported in my aforesaid U.S. Pat. No. 6,534,676, DITPA has been shown to improve left ventricular (LV) performance in post-infarction experimental models of heart failure when administered alone or in combination with an angiotension I-converting enzyme inhibitor. Cholesterol was significantly reduced in heart failure patients receiving DITPA after two and four weeks treatment, $P<0.05$ and $P<0.1$, respectively. In addition, it was noted that triglycerides were significantly reduced in these heart failure patients at two and four weeks of treatment with $P<0.05$ and $P<0.005$, respectively.

3,5-T$_2$ and DITPA differ only in the side chain attached to the inner phenolic ring. In each case, the side chain consists of 3 carbons, ending in an amino acid group in 3,5-T$_2$ and a carboxylic acid in DITPA. The structural similarity suggests the compounds should have some physiologic similarities. As reported in my aforesaid U.S. Pat. No. 6,534,676 normal volunteers and patients with heart failure indicate two such similarities: 1) There was significant weight loss in heart failure patients, who were obese and poorly conditioned, but no significant loss in volunteers who were more active and free of significant heart disease; and 2) Unexpectedly, there was a decrease not only in total cholesterol and LDL-cholesterol but also a highly significant decrease in triglycerides (P=0.005). A decrease in triglycerides also was seen with administration of 3,5-T$_2$, but to my knowledge, has not previously been reported either with thyroid replacement in hypothyroidism or in the case of thyroid hormone analogs [13].

SUMMARY OF THE INVENTION

The new and surprising effect I have found is that administration of 3,5-diiodothyropropionic acid (DITPA) not only reduces total cholesterol and low-density lipoprotein (LDL) cholesterol when it is administered to overweight euthyroid individuals, it stimulates weight loss, and also reduces triglycerides, particularly in overweight individuals.

Adipose tissue is the largest storehouse of energy in the body (in the form of triglycerides) and typically makes up 15-20% or more of the body weight in men and 20-25% or more of the body weight in women. Thyroid hormones exert a wide range of effects on lipid metabolism. In the thyrotoxic state lipid mobilization, synthesis and degradation are all accelerated. Degradation of most lipids is stimulated out of proportion to synthesis and as a consequence body lipid deposits are depleted. Thus, administration of DITPA is seen to stimulate weight loss and lower hypertriglyceridemia, particularly in overweight patients, and may be used to treat or to reduce risk of death or progression of coronary heart disease (CHD) in patients with metabolic syndrome.

DETAILED DESCRIPTION OF PREFERRED EMBODIMENTS

DITPA was synthesized following good manufacturing procedures by coupling dianisoleiodium trifluoroacetate with ethyl-3-(3,5-diiodo-4-hydroxyphenyl)-propionate followed by removal of the methyl and ethyl protective groups as described in my aforesaid U.S. Pat. No. 6,534,676.

The effects of administering DITPA were studied in 7 volunteers all but one of whom had normal weight. Study participants were men between the ages of 27 and 52 years. Of note, there was an average weight loss of only 0.6 kg for the group, or 0.7% of their initial weight, which did not attain statistical significant (P=0.13). Body Mass Index (BMI) was calculated as a meaning of judging obesity. BMI is a measure of body fat based on height and weight that applies to both men and women. Excluding the one overweight individual BMI ranged from 21.0 to 26.7 (average 25.0). (The range of normal weight for men is 20.7 to 26.4, marginally over weight 26.4 to 27.8, overweight 27.8 to 31.1, and very obese is greater than 31.1). BMI was calculated using the BMI calculator at the National Heart, Lung, and Blood Institute web site (nhlbisupport/com/bmi/). BMI and lipid data for the six volunteers of normal body weight are summarized in Table I A&B:

TABLE I (a)

Healthy Volunteers Treated with DITPA

| Initials | BMI (kg/m$^2$) |
|---|---|
| T. M. | 24.4 |
| T. V. | 24.4 |
| K. L. | 27.4 |
| A. M. | 26.7 |
| J. B. | 21.0 |
| R. F. | 26.1 |
| Mean | 25.0 |
| SE | 0.9 |

TABLE 1 (b)

Healthy Volunteers Treated with DITPA

| Initials | Cholesterol mg/dL | LDL-C mg/dL | HDL-C mg/dL | Triglycerides mg/dL |
|---|---|---|---|---|
| Baseline: | | | | |
| T M | 190 | 112.6 | 53 | 122 |
| T V | 181 | 119.6 | 25 | 182 |
| K L | 320 | | | 538 |
| A M | 191 | 160.4 | 9 | 108 |
| J B | 133 | 75.4 | 41 | 83 |
| R F | 198 | 139.8 | 37 | 106 |
| Mean | 202.2 | 121.6 | 33.7 | 189.8 |
| SE | 25.4 | 14.2 | 7.5 | 71.0 |
| After 2 weeks: | | | | |
| T M | 191 | 120.6 | 50 | 102 |
| T V | 141 | 86.8 | 31 | 116 |
| K L | 298 | 142.6 | 36 | 597 |
| A M | 164 | 102.2 | 28 | 169 |
| J B | 94 | 47.4 | 30 | 83 |
| R F | 149 | 90.2 | 38 | 104 |
| Mean | 172.8 | 98.3 | 35.5 | 195.2 |
| SE | 28.2 | 12.3 | 3.3 | 81.2 |
| After 4 weeks: | | | | |
| T M | 187 | 109.4 | 52 | 128 |
| T V | 122 | 71 | 27 | 120 |
| K L | 305 | 137 | 31 | 685 |
| A M | 168 | | | 106 |
| J B | 79 | | | 68 |
| R F | 182 | 118.2 | 45 | 94 |
| Mean | 173.8 | 108.9 | 38.8 | 200.2 |
| SE | 31.2 | 13.9 | 5.9 | 97.4 |

Cholesterol levels ranged from 133 mg/dL to 320 mg/dL (average 202.2±25.4 mg/dL), LDL-cholesterol 121.6±14.2, HDL-cholesterol 33.7±7.5. Triglycerides levels ranged from 83 mg/dL to 538 mg/dL (average 189.8±71.1 mg/dL) before treatment. On day 1, these normal volunteers were started on 1.875 mg/kg DITPA in two divided doses per day. This treatment regimen was continued for two weeks. At the end of the second week, the dose was doubled to 3.75 mg/kg and the volunteers were treated for two additional weeks.

After two weeks of treatment with DITPA cholesterol levels were decreased to an average of 172.8±28.2 mg/dL, LDL-cholesterol to 98.3±13.3 mg/dL. HDL-cholesterol and triglycerides were unchanged at 35.5±3.3 mg/dL and 195.2±81.2 mg/dL, respectively. After four weeks of treatment cholesterol, LDL-cholesterol, HDL-cholesterol and triglyceride levels were essentially unchanged from values after 2 weeks of treatment. Note that triglyceride levels in the one individual (K. L.) with very high triglyceride levels, was unaffected by treatment. Thus treatment with DITPA in individuals of normal body weight lowered cholesterol and LDL-cholesterol but did not cause weight loss or a decrease in triglycerides.

Treatment was repeated with a second group of 8 patients with heart failure. (One patient with heart failure treated with DITPA reported in U.S. Pat. No. 6,716,877 was excluded because no lipid data were available at baseline.) Those in the second group had Body Mass Indices ranging from 21.0 to 30.3 (average 32.2, which was in the obese range). The patients in this group received an initial dose of 1.875 mg/kg for two weeks, which was doubled to 3.75 mg/kg for two additional weeks. As reported earlier, heart failure patients receiving DITPA experienced an average weight loss of 4 kg or 4.0% of their initial body weight (P=0.059).

TABLE II (a)

Heart Failure Patients Treated with DITPA

| Initials | BMI (kg/m$^2$) |
|---|---|
| R. V. | 45.5 |
| J. G. | 36.2 |
| F. R. | 28.1 |
| E. C. | 30.2 |
| J. D. | 30.0 |
| J. F. | 31.3 |
| W. P. | 36.9 |
| C. H. | 23.9 |
| Mean | 31.5 |
| SE | 2.4 |

TABLE II (b)

Heart Failure Patients Treated with DITPA

| Initials | Cholesterol mg/dL | LDL-C mg/dL | HDL-C mg/dL | Triglycerides mg/dL |
|---|---|---|---|---|
| Baseline: | | | | |
| R. V. | 195 | 141 | 27 | 133 |
| J. G. | 217 | 104 | 23 | 449 |
| F. R. | 102 | 48 | 30 | 119 |
| E. C. | 144 | 62 | 38 | 219 |
| J. D. | 186 | 94 | 28 | 321 |
| J. F. | 241 | 167 | 48 | 128 |
| W. P. | 168 | 89 | 31 | 238 |
| C. H. | 233 | 152 | 37 | 222 |
| Mean | 185.8 | 107.1 | 32.8 | 228.6 |
| SE | 16.6 | 15.1 | 2.8 | 39.8 |
| After 2 weeks: | | | | |
| R. V. | 161 | 107 | 30 | 120 |
| J. G. | 150 | 88 | 20 | 208 |
| F. R. | 106 | 55 | 27 | 119 |
| E. C. | 128 | 50 | 32 | 228 |
| J. D. | 176 | 88 | 28 | 300 |
| J. F. | 244 | 177 | 41 | 131 |
| W. P. | 177 | 81 | 34 | 312 |
| C. H. | 190 | 99 | 28 | 317 |
| Mean | 166.5 | 93.1 | 30.0 | 216.9 |
| SE | 14.8 | 13.9 | 2.1 | 30.6 |
| After 4 weeks: | | | | |
| R. V. | 143 | 102 | 26 | 77 |
| J. G. | 125 | 69 | 20 | 179 |
| F. R. | 83 | 43 | 26 | 69 |
| E. C. | 107 | 41 | 31 | 176 |
| J. D. | 144 | 77 | 26 | 205 |
| J. F. | 243 | 172 | 52 | 93 |
| W. P. | 127 | 68 | 32 | 135 |
| C. H. | 189 | 102 | 36 | 253 |
| Mean | 145.1 | 84.3 | 31.1 | 148.4 |
| SE | 17.7 | 14.9 | 3.4 | 23.3 |

At baseline average cholesterol values were 185.8±16.6 mg/dL, LDL-cholesterol 107.1±15.1 mg/dL, HDL-cholesterol 32.8±2.8 mg/dL and triglycerides 228.6±39.8 mg/dL. After two weeks of treatment with DITPA cholesterol decreased to 166.5±14.8 mg/dL, LDL-cholesterol to 93.1±13.9 mg/dL and triglycerides to 216.9±30.6 mg/dL. After four weeks of treatment cholesterol decreased to 145.1±17.7, LDL-cholesterol to 84.3±14.9 and triglycerides to 148.4±23.3. The decrease in triglycerides of 35% is comparable to that reported by Goglia and Lanni in normal volunteers treated with 3,5-$T_2$. Of particular interest, the two patients (J. G. and J. D.), with triglycerides of greater than 300, had decreases in triglycerides of 60% and 36%, respectively.

It is thus seen that administration of DITPA caused a greater decrease in weight of overweight individuals than those of normal body weight. Triglycerides also were decreased to a greater extent in overweight individuals. In these individuals, the triglycerides were decreased both in those with normal and elevated triglycerides levels.

As used herein, the terms "overweight individuals" and "overweight patients" are those individuals or patients having a Body Mass Index of 30 or more.

As used herein, "therapeutically effective amounts" or "effective dose levels" for achieving weight loss and lowering of triglyceride levels of overweight individuals were 0.1 to 10.0 mg/kg daily, preferably 1.875 to 3.75 mg/kg daily. Preferably, the daily doses were divided in half and administered twice daily.

While the invention has been described in detail in treating humans in accordance with certain preferred embodiments the invention also advantageously may be used for treating overweight animals such as dogs and cats, and other domesticated animals. Also, while administration of DITPA appears to reduce triglycerides, particularly in overweight individuals, individuals of normal weight also may benefit by a reduction of triglycerides from administration of DITPA in accordance with the present invention. Moreover, DITPA advantageously may be combined with one of the conventional lipid/triglyceride lowering therapeutic agents such as HMG CoA reductase inhibitors commonly referred to as 'statins', e.g., atorvastatin (Lipitor), simvastatin (Zocor), fluvastatin (Lescol), lovastatin (Mevacor), rosuvastatin (Crestor), and pravastatin (Pravachol) or the like. Niacin and inhibitors of cholesterol absorption such as ezetimibe (Zetia) also may be combined with DITPA. For treatment of hypertriglyceridemia fibric acid derivative such as gemfibrozil (Lopid), fenofibrate (Tricor), etc. may be combined with DITPA. Still other modifications and changes therein may be made without departing from the spirit and scope of the invention.

APPENDIX

REFERENCES

1. Ford E S, Giles W H, Dietz W H: Prevalence of the metabolic syndrome among US adults. Findings from the third national health and nutrition examination survey. JAMA 287:356-359, 2002
2. Mason R L, Hunt H M, Hurxthal L M: Blood cholesterol values in hyperthyroidism and hypothyroidism: their significance. N Eng J Med 203:1273-1278, 1930
3. Peters J P, Man E B: The significance of serum cholesterol in thyroid disease. J Clin Invest 29:1-11, 1950

4. Ladenson P W, Goldenheim P D, Ridgway E C: Rapid pituitary and peripheral tissue responses to intravenous L-triiodothyronine in hypothyroidism. J Clin Endocrinol Metab 56:1252-1259, 1983.
5. *The Thyroid. A Fundamental and Clinical Text.* 6$^{th}$ Ed., Editors: L. E. Braverman and R. D. Utiger, J. B. Lippincott Co., pp. 489-490.
6. Walton K W, Campbell D A, Tonks E L: The significance of alterations in serum lipids in thyroid dysfunction. I. The relation between serum lipoprotein, carotenoids and vitamin A in hypothyroidism and thyrotoxicosis. Clin Sci 29:199-215, 1965.
7. Walton K W, Scott P J, Dykes P W, Davies J W: The significance of alternations in serum lipids in thyroid dysfunction. II. Alterations of metabolism and turnover of 131-I-low-density lipoproteins in hypothyroidism and thyrotoxicosis. Clin Sci 29:217-238
8. Abrams J J, Grundy S M: Cholesterol metabolism in hypothyroidism and hyperthyroidism in man. J Lipid Res 22:323-338, 1981.
9. Staels B. Van Tol A, Chan L, Will H M, Verhoeven G A, Auwerx J: Alterations in thyroid status modulate apolipoprotein, hepatic triglyceride lipase, and low-density lipoprotein receptor in rats. Endocrinology 127:1145-1152.
10. Salter A M, Hayashi R, Al-Seeni M, Brown N F, Bruce J, Sorensen O, et al.: Effects of hypothyroidism and high-fat feeding on mRNA concentrations for the low-density lipoprotein receptor and on acyl-CoA:cholesterol acyltransferase activities in rat liver. Biochem J 276:825-832, 1991.
11. Packer C J, Shepard J, Lindsay G M, Gaw A, Taskinen M R: Thyroid replacement therapy and its influence on postheparin plasma lipases and apolipoprotein-β metabolism in hypothyroidism. J Clin Endocrinol Metab 76:1209-1216, 1993.
12. Moreno M, Lanni A., Lombardi A, Goglia F: How the thyroid controls metabolism in the rat: different roles for triiodothyronine and diiodothyronines. J Physiol (London) 505:529-538, 1997.
13. Morkin E, Ladenson P, Goldman S, Adamson C: Thyroid hormone analogs for treatment of hypercholesterolemia and heart failure: past, present and future prospects. J Mol Cell Cardiol 37:1137-1146, 2004.

The invention claimed is:

1. A method for stimulating weight loss in an overweight animal comprising administering to the animal a therapeutically effective amount of 3,5-diiodothyropropionic acid.

2. The method of claim 1, wherein 3,5-diiodothyropropionic acid is administered as a formulation selected from the group consisting of a liquid preparation, a solid preparation, a capsule preparation, and an implant preparation.

3. The method of claim 2, wherein said formulation further comprises a pharmaceutically acceptable carrier.

4. The method of claim 3, wherein said formulation further comprises at least one of a stabilizer, an excipient, a solubilizer, an antioxidant, a pain-alleviating agent, and an isotonic agent.

5. The method of claim 1, wherein said 3,5-diiodothyropropionic acid is administered by parenteral injection.

6. The method of claim 5, wherein said 3,5-diiodothyropropionic acid is administered by parenteral intravenous injection.

7. The method of claim 1, wherein said 3,5-diiodothyropropionic acid is administered orally.

8. The method of claim 1, wherein said 3,5-diiodothyropropionic acid is administered directly to the pulmonary system of the animal.

9. The method of claim 1, wherein said 3,5-diiodothyropropionic acid is administered transdermally.

10. The method of claim 1, wherein said 3,5-diiodothyropropionic acid is administered by implantation.

11. The method of claim 1, wherein the animal comprises a human.

12. The method of claim 1, wherein the animal comprises a domesticated animal.

13. The method of claim 1, wherein said 3,5-diiodothyropropionic acid is administered at a daily dosage of 0.1 to 10.0 mg/kg.

14. The method of claim 13, wherein said daily dosage is from 1.875 to 3.75 mg/kg.

15. The method of claim 1, wherein said 3,5-diiodothyropropionic acid is administered together with a conventional lipid lowering therapeutic agent.

16. A method for lowering triglyceride levels of a patient, comprising administering to the patient a therapeutically effective amount of 3,5-diiodothyropropionic acid.

17. The method of claim 16, wherein the patient is an overweight patient.

18. The method of claim 16, wherein 3,5-diiodothyropropionic acid is administered as a formulation selected from the group consisting of a liquid preparation, a solid preparation, a capsule preparation, and an implant preparation.

19. The method of claim 16, wherein said formulation further comprises a pharmaceutically acceptable carrier.

20. The method of claim 19, wherein said formulation further comprises at least one of a stabilizer, an excipient, a solubilizer, an antioxidant, a pain-alleviating agent, and an isotonic agent.

21. The method of claim 16, wherein said 3,5-diiodothyropropionic acid is administered by parenteral injection.

22. The method of claim 21, wherein said 3,5-diiodothyropropionic acid is administered by parenteral intravenous injection.

23. The method of claim 17, wherein said 3,5-diiodothyropropionic acid is administered orally.

24. The method of claim 17, wherein said 3,5-diiodothyropropionic acid is administered directly to the pulmonary system of the patient.

25. The method of claim 17, wherein said 3,5-diiodothyropropionic acid is administered transdermally.

26. The method of claim 17, wherein said 3,5-diiodothyropropionic acid is administered by implantation.

27. The method of claim 17 wherein said 3,5-diiodothyropropionic acid is administered at a daily dosage of 0.1 to 10.0 mg/kg.

28. The method of claim 25, wherein said daily dosage is from 1.875 to 3.75 mg/kg.

29. The method of claim 17, wherein said 3,5-diiodothyropropionic acid is administered with a conventional liquid lowering therapeutic agent.

* * * * *